(12) United States Patent
Bryce et al.

(10) Patent No.: US 12,243,628 B2
(45) Date of Patent: Mar. 4, 2025

(54) DATA PROCESSING SYSTEMS AND METHODS FOR IDENTIFYING NEW INDICATIONS FOR DRUGS

(71) Applicant: Sanofi, Paris (FR)

(72) Inventors: Paul Bryce, West Newton, MA (US); Emanuele de Rinaldis, Cambridge, MA (US); Ramon Antonio Hernandez Vecino, Paris (FR); Francisco Javier Jimenez Jimenez, Brookline, MA (US); Cliona Marie Molony, Boston, MA (US); Anne-Gaëlle Radenac, Cambridge, MA (US)

(73) Assignee: Sanofi, Paris (FR)

( * ) Notice: Subject to any disclaimer, the term of this patent is extended or adjusted under 35 U.S.C. 154(b) by 589 days.

(21) Appl. No.: 17/116,995

(22) Filed: Dec. 9, 2020

(65) Prior Publication Data

US 2021/0174912 A1 Jun. 10, 2021

Related U.S. Application Data

(60) Provisional application No. 62/945,814, filed on Dec. 9, 2019.

(30) Foreign Application Priority Data

Jun. 9, 2020 (EP) ..................... 20315299

(51) Int. Cl.
*G16H 40/20* (2018.01)
*G06N 20/00* (2019.01)
(Continued)

(52) U.S. Cl.
CPC ............. *G16H 10/20* (2018.01); *G06N 20/00* (2019.01); *G16H 50/70* (2018.01)

(58) Field of Classification Search
CPC ......... G16H 10/20; G16H 50/70; G06N 20/00
See application file for complete search history.

(56) References Cited

U.S. PATENT DOCUMENTS

| | | | |
|---|---|---|---|
| 11,723,974 B2 | 8/2023 | Bryce et al. | |
| 2011/0082712 A1* | 4/2011 | Eberhardt, III | ........ G06Q 40/08 705/4 |

(Continued)

FOREIGN PATENT DOCUMENTS

| | | |
|---|---|---|
| JP | 2012-025763 A | 2/2012 |
| JP | 2016-099674 A | 5/2016 |

OTHER PUBLICATIONS

Burgel, Co-morbidities in Chronic Obstructive Pulmonary Disease From Assessment to Treatment, 2014 (Year: 2014).*

(Continued)

*Primary Examiner* — Bion A Shelden
*Assistant Examiner* — Shyam M Goswami
(74) *Attorney, Agent, or Firm* — Fish & Richardson P.C.

(57) ABSTRACT

Data processing systems for identifying new indications for a drug can include a computer-readable memory including computer-executable instructions; and at least one processor configured to execute executable logic including the computer-executable instructions and at least one machine learning model to perform one or more operations. The one or more operations can include receiving data representing medical records of a plurality of patients; selecting a set of patients; determining a plurality of patient characteristics of the set of patients; grouping, in accordance with the plurality of patient characteristics, the set of patients to generate a plurality of distinct groups, each of the distinct groups including at least one patient of the set of patients; selecting, based on one or more group selection criteria, a set of distinct groups of the plurality of distinct groups; and (Continued)

identifying one or more relevant patient characteristics by analyzing each distinct group of the set of distinct groups.

16 Claims, 5 Drawing Sheets

(51) Int. Cl.
    *G16H 10/20*     (2018.01)
    *G16H 50/70*     (2018.01)

(56) References Cited

U.S. PATENT DOCUMENTS

| | | | |
|---|---|---|---|
| 2012/0296090 A1 | 11/2012 | Wong et al. | |
| 2015/0080703 A1* | 3/2015 | Reiman | G01N 33/6896 600/409 |
| 2016/0196398 A1* | 7/2016 | Vivero | G16H 15/00 705/2 |
| 2018/0166175 A1* | 6/2018 | Shah | G16H 70/40 |
| 2019/0096526 A1 | 3/2019 | Hirsch et al. | |
| 2019/0350912 A1 | 11/2019 | Zhang et al. | |
| 2021/0220470 A1 | 7/2021 | Bryce et al. | |

OTHER PUBLICATIONS

Danov, et. al., "Human lung tissue provides highly relevant data about efficacy of new anti-asthmatic drugs" Nov. 30, 2018 (Year: 2018).*
Burgel, et. al., "Identification of Clinical Phenotypes Using Cluster Analyses in COPD Patients with Multiple Comorbidities" Feb. 10, 2014 (Year: 2014).*
International Preliminary Report on Patentability in International Appln. No. PCT/US2020/064100, dated Jun. 23, 2022, 16 pages.
PCT International Search Report and Written Opinion in International Application No. PCT/US2020/064100, dated Apr. 1, 2021, 23 pages.
Xu et al., "Validating drug repurposing signals using electronic health records: a case study of metformin associated with reduced cancer mortality", Journal of the American medical Informatics Association, Jul. 2014, 22(1):179-191.
Yella et al., "Changing Trends in Computational Drug Repositioning", Pharmaceuticals, Jun. 2018, 11(2):57, 21 pages.

* cited by examiner

DATA PROCESSING SYSTEMS AND METHODS FOR IDENTIFYING NEW INDICATIONS FOR DRUGS

CLAIM OF PRIORITY

This application claims the benefit of European Patent Application 20315299.6, filed Jun. 9, 2020 and U.S. Provisional Patent Application Ser. No. 62/945,814, filed on Dec. 9, 2019. The entire contents of the foregoing are hereby incorporated by reference.

FIELD OF THE INVENTION

This disclosure generally relates to data processing systems and methods for identifying new indications for drugs.

BACKGROUND

Identifying new drug indications may refer to a strategy for drug discovery that can be relatively low-cost and can provide high efficiency. Identifying new indications for a drug typically involves analyzing whether a drug that has been approved for treating one type of condition (e.g., diseases) can be used to treat other types of conditions (e.g., common and/or rare diseases). Several therapeutic areas present high potential for identifying new indications, including oncology, immunology, infectious diseases and orphan diseases.

SUMMARY

In at least one aspect of the present disclosure, a data processing system is provided. The data processing system includes a computer-readable memory comprising computer-executable instructions and at least one processor configured to execute executable logic including the computer-executable instructions and at least one machine learning model. When the at least one processor is executing the computer-executable instructions, the at least one processor is configured to carry out one or more operations. The one or more operations include receiving data representing medical records of a plurality of patients. The one or more operations include selecting, based on the medical records, a set of patients by: determining at least one target signaling pathway associated with the drug; and determining one or more indicators based on one or more factors corresponding to a diagnosis linked to the target signaling pathway. The one or more operations include determining a plurality of patient characteristics of the set of patients, each patient of the set of patients exhibiting at least one of the plurality of patient characteristics. The one or more operations include grouping, using the machine learning model and in accordance with the plurality of patient characteristics, the set of patients to generate a plurality of distinct groups, each of the distinct groups including at least one patient of the set of patients. The one or more operations include selecting, based on one or more group selection criteria, a set of distinct groups of the plurality of distinct groups. The one or more operations include identifying one or more relevant patient characteristics by analyzing each distinct group of the set of distinct groups.

The machine learning model can be trained to group the set of patients using one or more unsupervised clustering techniques. The one or more unsupervised clustering techniques can include a bisecting k-means clustering technique. Grouping the set of patients can include performing multiple correspondence analysis to reduce dimensions of the plurality of patient characteristics.

Selecting the set of distinct groups can include determining, for each distinct group of the plurality of distinct groups, a feature score for each patient characteristic exhibited by that distinct group. Selecting the set of distinct groups can include comparing the feature score of each distinct group of the plurality of distinct groups to a feature score threshold. Selecting a set of distinct groups can include at least one of: determining a stability measure for each distinct group of the plurality of distinct groups, determining a purity measure for each distinct group of the plurality of distinct groups, and determining a number of patients of the set of patients included in each distinct group of the plurality of distinct groups.

Identifying the one or more relevant patient characteristics can include generating a plurality of potentially relevant patient characteristics by, for each distinct group of the set of distinct groups, selecting the patient characteristics of the plurality of patient characteristics that are exhibited by that distinct group and correspond to a theme of that group. Identifying the one or more relevant patient characteristics can include ranking each of the potentially relevant patient characteristics of the plurality of potentially relevant patient characteristics. Ranking each of the potentially relevant patient characteristics can include, for each potentially relevant patient characteristic, assigning a rank value based on a frequency of co-occurrence of that potentially relevant patient characteristic and at least one referential indication associated with the drug. The co-occurrence can be measured by determining, for each of the potentially relevant patient characteristics, a proportion of the set of distinct groups that comprises both that potentially relevant patient characteristic and the at least one referential indication. Identifying the one or more relevant patient characteristics can include determining, for each of the potentially relevant patient characteristics, at least one of: a clinical feasibility and a commercial feasibility The one or more operations can include identifying at least one of the one or more relevant patient characteristics as a target indication for the drug.

These and other aspects, features, and implementations can be expressed as methods, apparatus, systems, components, program products, means or steps for performing a function, and in other ways.

Implementations of the present disclosure can provide one or more of the following advantages. When compared with conventional technology, the systems and methods described in this specification can improve computational efficiency by, for example, reducing the computational time for processing large amounts of data having different levels of complexity for identifying potentially relevant indications (sometimes referred to as patient characteristics in this specification) for drugs. Particular machine learning techniques can be used to discover new indications that may not be identified by conventional technology. When compared with conventional technology, the systems and methods described in this specification can reduce the reliance on human input and skill.

These and other aspects, features, and implementations will become apparent from the following descriptions, including the claims.

DETAILED DESCRIPTION

Figure 1:
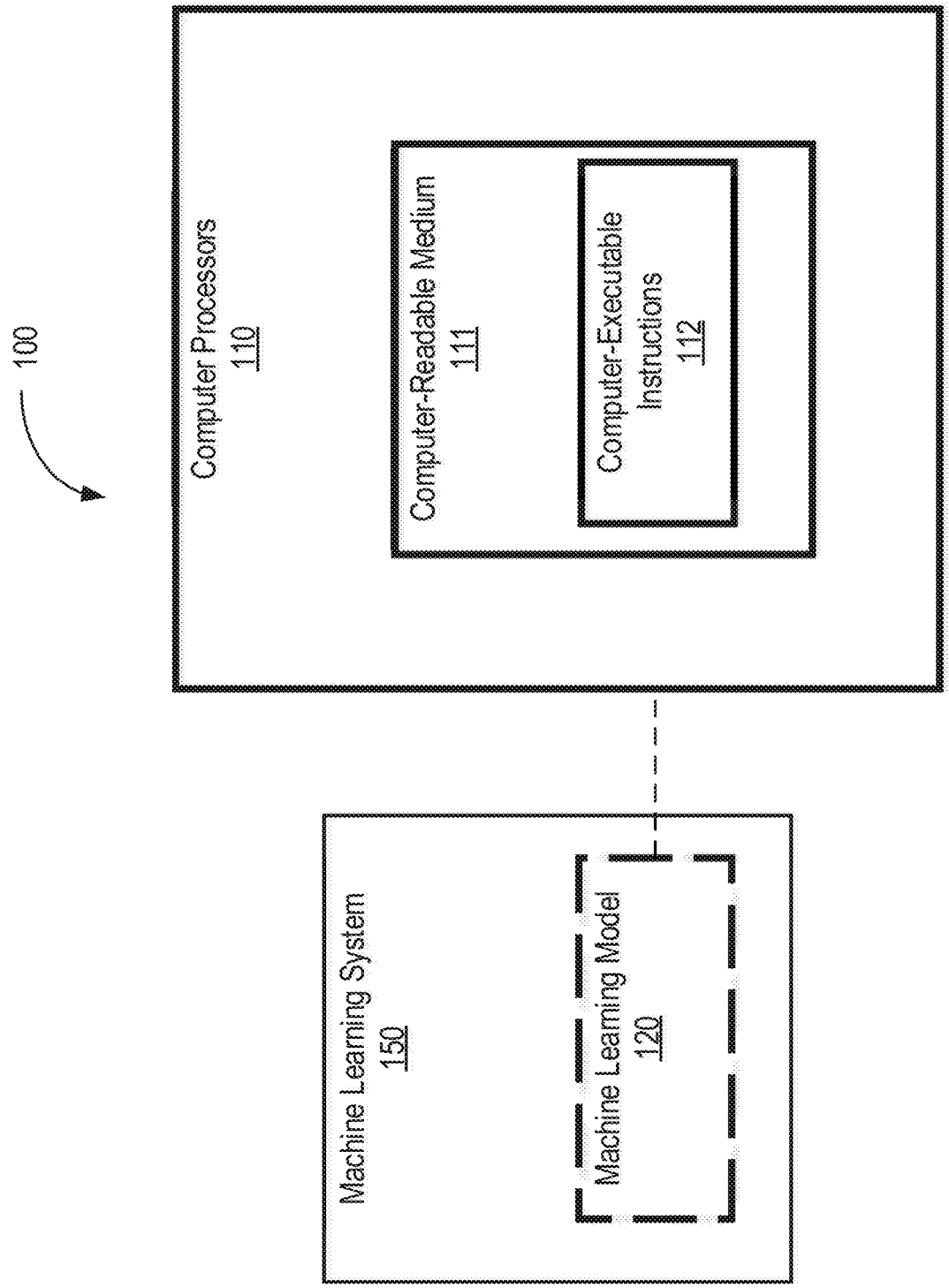
FIG. 1 is a diagram illustrating an example of a data processing system for identifying new indications for a drug.

New clinical indications (e.g., a reason to use a drug) can be found for clinically approved drugs. As hundreds of new indications are explored, key opinion leaders (KOL) may not be able to handle the high level of complexity corresponding to these new indications. Processing large amounts of data and using advanced analytics can support KOL-centric approaches. Guided by relevant clinical questions, powerful advanced analytics techniques can mine clinically relevant information hidden in large amounts of data, which can then assist clinical decision making.

Computational methods for identifying new indications for drugs can use similarity measures (chemical similarity, molecular activity similarity, gene expression similarity, or side effect similarity), molecular docking, or shared molecular pathology to detect new drug-disease relationships. Approaches for identifying new indications for drugs can be classified as network-based, text mining (literature search), and semantic approaches.

Network-based approaches can involve creating integrated networks by combining multiple data sources such as drugs, proteins, genes and diseases. For example, a Connectivity Map (C-Map) approach can exploit the transcriptome, by utilizing gene expression profiling to connect biology, chemistry and clinical conditions to facilitate the discovery of new disease-gene-drug connections. A network-based cluster approach (Clustering) can be used to find biological modules. This approach is inspired by the fact that biologic entities (disease, drug, protein, etc.) in the same module of biological networks typically share similar characteristics. Clustering can involve finding drug-disease, drug-drug, disease-disease, or drug-target relationships using the topology structures of networks. There can be some difficulties involved with implementing a clustering approach. For example, edges linking drugs and diseases may depend on collected drug-disease associations that are incomplete, which may require integration of multiple databases to improve the accuracy of the prediction. In addition, incorporating different data sources that offer information about a drug's side effects can allow for the collection of potential safety signals. Moreover, it may be difficult to differentiate between negative and positive associations and no "gold" standard method exists to test associations among biological modules.

Text mining based approaches can use keyword co-occurrences and semantic inferences for new drug-disease associations. Some approaches can be based on Swanson's analogical reasoning approach (the ABC model), which may assume that if 'B' is one of the characteristics of disease 'C', and that substance 'A' affects 'B', then the implicit link 'A:C' through the B-connection can be deduced. However, literature mining based methods, alone, may be limited due to the ambiguous nature of language, a limited coverage of biomedical relationships, and a limited accuracy of text mining techniques.

Implementations of the data processing systems and methods described in this specification can alleviate the previously mentioned disadvantages by using a real-world data driven protocol for in order to identify new indications for drugs. In some implementations, the data processing systems and methods described in this specification combine analytics and real-world data with KOL clinical output. In some implementations, the data processing systems and methods described in this specification use real-world data and analytics in an unsupervised manner. In some implementations, patients are clustered using machine learning techniques, and groups of conditions appearing across multiple clusters are identified. In some implementations, the identified groups of conditions potentially correspond to a common biological pathway. The data processing systems and methods described in this specification can be used to identify potential indications that have not been previously identified using conventional techniques.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

Example Data Processing Systems and Methods

FIG. 1 shows an example of a data processing system 100. In some implementations, the data processing system 100 is configured to process data that can represent medical records of a plurality of patients to identify new indications of a drug. The system 100 includes computer processors 110. The computer processors 110 include computer-readable memory 111 and computer readable instructions 112. The system 100 also includes a machine learning system 150. The machine learning system 150 includes a machine learning model 120. The machine learning model 120 can be separate from or integrated with the computer processors 110.

The computer-readable medium 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 111 includes code-segments having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code such as the computer-executable instructions 112 and configured to execute executable logic that includes the machine learning model 120.

The computer processors 110 are configured to receive data representing medical records of a plurality of patients. For example, the computer processors 110 can receive data from a database that includes electronic medical records (EMRs) data for approximately 94 million patients (or more) identifiable by a key identifier (ID) that allows matching of patients across different data tables. In some implementations, the data indicates diagnoses, lab tests, procedures, medications, patient events, insurance, biomarkers, measurements, clinical status, lifestyle parameters, microbiology, prescriptions, and so forth. In some implementations, the data includes natural language process driven data. The data can be received through any of various techniques, such as wireless communications, optical fiber communications, USB, CD-ROM, and so forth.

The machine learning system 150 is capable of applying machine learning techniques to train the machine learning model 120. As part of the training of the machine learning model 120, the machine learning system 150 can form a training set of input data by identifying a positive training set of input data items that have been determined to have the property in question, and, in some implementations, can form a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 150 applies dimensionality reduction to reduce the amount of data in the feature vectors for the input data to a smaller, more representative set of data. For example, the machine learning system 150 can apply multiple correspondence analysis (MCA), linear discriminant analysis (LDA), principle component analysis (PCA), and so forth.

In some implementations, the machine learning system 150 uses unsupervised machine learning to train the machine learning model 120. Typically, unsupervised machine learning techniques make inferences from datasets using input vectors without referring to known, or labelled, outcomes. In some implementations, the machine learning system 150 can perform clustering to divide data points into a number of groups such that the data points in the same group are more similar to other data points in the same group and dissimilar to data points in other groups. In some implementations, clustering includes performing K-means clustering, in which a one-level unnested partitioning of data points is created by iteratively partitioning the data set. That is, if K is the desired number of clusters, in each iteration, the data set is partitioned into K disjoint clusters. The processes can be continued until a specified clustering criterion function value is optimized. In some implementations, the machine learning system 150 is configured to perform bisecting K-means clustering. Bisecting k-means clustering typically involves splitting one cluster into two subclusters at each bisecting step (e.g., by using k-means) until k clusters are obtained. Bisecting K-means clustering may be more beneficial when compared to K-means clustering, as bisecting K-means clustering can reduce computation time when K is a relatively large value, can produce clusters of similar size, and can produce clusters with smaller entropy.

The computer processors 110 are configured to execute the computer-executable instructions 112 to perform one or more operations. In some implementation, the one or more operations include receiving data representing medical records of a plurality of patients. For example, the computer processors 110 can receive data from a database that includes electronic medical records (EMRs) for approximately 94 million patients (or more) identifiable by a key identifier (ID) that allows matching of patients across different data tables. In some implementations, the data indicates diagnosis, lab test, procedures, medications, patient events, insurance, biomarkers, measurements, clinical status, lifestyle parameters, microbiology, prescriptions, and so forth. In some implementations, the data includes natural language process driven data. The data can be received through any of various techniques, such as wireless communications, optical fiber communications, USB, CD-ROM, and so forth.

In some implementations, the one or more operations include selecting, based on the medical records, a set of patients. Selection of the set of patients includes determining at least one target signaling pathway associated with a drug for which new indications are to be identified. For example, if the drug is Dupilumab, the computer processors 110 may determine that the drug modulates the interleukin 4 (IL-4) and interleukin 13 (IL-13) signaling pathway based on known functions of the drug. Selecting the set of patients also includes determining one or more indicators based on one or more factors corresponding to a diagnosis linked to the target signaling pathway. For example, factors such as pathway mechanisms, related clinical conditions, therapeutic analogues, data and epidemiology, and pharmaceutical life-cycle management alignment can be used to search through sources that include medical databases and medical evidence software to identify diseases linked to the determined signaling pathway. These diseases can be categorized based on the strength of the link to the determined signaling pathway. The categories can include a focused group, a medium group, and a broad group. For example, returning to the IL-4/IL-13 example, a focused group of diseases can include diseases that have a direct relationship with the IL-4/IL-13 mechanism of action on the Th2 pathway, a medium group of diseases can include diseases that have an indirect relationship with the IL-4/IL-13 mechanism of action on the Th2 pathway, and a broad group of diseases can include diseases associated with a broader inflammatory response. Moving from the focus group to the broad group can increase the number of indicators to be considered when selecting the set of patients and can reduce the likelihood of molecule impact. Accordingly, in some implementations, only the focused group, or the focused and medium group, are used to select the set of patients. In some implementations, only patients with at least one diagnosis, medication, lab test, and/or procedure associated with the determined signaling pathway are selected for inclusion into the set of patients. A detailed example of factors and indicators is provided later with reference to Table 1.

In some implementations, the one or more operations include determining a plurality of patient characteristics (sometimes referred to as features in this specification) of the set of patients, in which each patient of the set of patients exhibits at least one of the plurality of patient characteristics. Determining the plurality of patient characteristics can include analyzing the initially received data to identify broad patient characteristics to capture all or a substantial portion of the received data. For example, the broad patient characteristics can correspond to diagnoses (e.g., immuno-conditions, diabetes), prescriptions (e.g., immuno-drugs, other drug classes), procedures (e.g., human leukocyte antigen typing), and laboratory results (e.g., IgE abnormal high/low). In some implementations, determining the plurality of patient characteristics includes receiving user input (e.g., through a user interface in communication with the computer processors 110). For example, a user can input patient characteristics based on clinical input, demographics, medication, comorbidities, procedures, and laboratory test data specific to immunology. Bespoke characteristic classes may also be added to increase data completeness, representativeness, and to collect more information on diseases and drug response. In some implementations, determining the plurality of patient characteristics includes validating the plurality of patient characteristics. Validating can include determining whether the patient characteristics of the initially received data are mapped correctly to the selected set of patients by calculating the percentage of selected patients with at least one of each characteristic family (e.g., the percentage of patients with a prescription record) and comparing this percentage to the percentage of patients of the initially received data with at least one of each characteristic family. The two numbers being closer in value indicates that the mapping has been done correctly. Validating can include determining whether the patient characteristics have been mapped to the correct patient by identifying a number of patients that are included in both the initially received data and the selected set of patients to verify identical mapping of patient characteristics between the patients of the initially received data and the selected set of patients.

In some implementations, the one or more operations include grouping, in accordance with the plurality of patient characteristics (e.g., as defined by features related to the determined signaling pathway), the set of patients to generate a plurality of distinct groups in which each of the distinct groups includes at least one patient of the set of patients. For example, the one or more computer processors 110 can execute the machine learning model 120 to perform a clustering technique, such as the bisecting k-means clustering technique described above. The clustering can result in a plurality of clusters (e.g., distinct groups) of patients in which patients in one cluster are more similar to each other than patients in other clusters with respect to their corresponding patient characteristics. In some implementations, the generated clusters may show correlations among patient characteristics, even if they weren't present in the same patient. Clinical inputs can be received and used in various stages of the clustering process to ensure the clinical relevance of the resulting clusters. For example, disease experts' clinical inputs can facilitate the creation of clinically relevant cohorts, in the inclusion and grouping of clinically relevant features, and in validating and assessing the clusters. Patient characteristics can be identified as being distinctive in clusters if they occurred more frequently than in the general population (e.g., overall in the selected set of patients).

In some implementations, Multiple Correspondence Analysis (MCA) is used to reduce the dimensions of the patient characteristics. Bisecting K-means can facilitate an appropriate and effective separation of patients with sufficiently "tight" but stable clusters, and allow a large number of clusters that exhibited immuno-relatedness to be used for scoring the patient characteristics, which is explained later in more detail. The resulting clusters can be presented (e.g., through a user interface) to users (e.g., clinical experts) for validation and assessment. This can reduce the risk of non-interpretability of the clusters and to ensure the absence of overlapping features between the different clusters.

In some implementations, the one or more operations include selecting, based on one or more group selection criteria, a set of distinct groups of the plurality of distinct groups. In some implementations, selecting the set of distinct groups includes ranking the groups and selecting a number of the most highly ranked groups (e.g., the top 60 ranked groups). The groups can be ranked based on immunology enrichment, stability, purity, and size. In some implementations, one or more measures (sometimes referred to as feature scores in this specification) are calculated for each patient characteristic to rank the clusters. The one or more measures can include, for example, distinctiveness (sometimes referred to as "lift score" in this specification), the number of patients within a cluster that present the patient characteristic, and an immunology score. The distinctiveness score measures how distinctive a patient characteristic is within a cluster versus the rest of the population (e.g., if males represent 50% of the population and 75% of the cluster, then the "lift score" can be equal to 1.5). In some implementations, only patient characteristics with a lift score that exceeds a threshold lift score (e.g., 1) and appearing in a percentage of patients that exceeds a threshold percentage of patients (e.g., 10%) are considered to define clusters and correspond to a theme of the clusters. Patient characteristics that are considered to define a cluster may be referred to as potentially relevant patient characteristics in this specification. The patient characteristics (e.g., either the patient characteristics considered to define clusters or all of the patient characteristics) can then be given an immunology score, which scores the patient characteristics according to its type (e.g., disease, drug, laboratory test, procedure, and so forth) and immunology relevance. The patient characteristic scores within each cluster can then be aggregated (e.g., summed) and normalized. Clusters meeting a threshold cluster score (e.g., 50%) can then be considered as immunology-specific.

Selecting the set of distinct groups can include assessing one or more of the stability, purity, and the number of patients within each cluster. Stability can be assessed using one or more of the following methods: (1) reproducing the clusters on different sizes of data; (2) changing the initializing seeds of the clusters; (3) changing the number of clusters produced and (4) applying a training-test method. For each cluster in the training set, stability can be defined as the maximum proportion of patients that are also grouped together in the test set. Purity can be measured by the intra-cluster variance of MCA components of patients within a cluster, which can result in homogenous and dense clusters. In some implementations, a cluster is selected if it exceeds a threshold stability percentage (e.g., 50%) and exceeds a threshold purity percentage (e.g., the cluster is in the highest 20% of purity among all clusters).

In some implementations, the one or more operations include identifying one or more relevant patient characteristics (e.g., indications) by analyzing each distinct group of the set of distinct groups. Identifying one or more relevant patient characteristics can include ranking the patient characteristics presented by each selected cluster (e.g., all of the patient characteristics or the patient characteristics considered to define a cluster). The ranking can be based on the frequency of co-occurrence with each a number of established (reference) characteristics (referential) of the drug for which new indications are to be identified (e.g., if the drug is Dupilumab, the reference characteristics may include asthma, atopic dermatitis, IgE allergy, and a composite immunology score). The co-occurrence can be measured by calculating the proportion of patient-weighted clusters that contain both the patient characteristic and the referential. In some implementations, one or more patient characteristics judged by subject-matter experts as relevant to the core cluster theme (e.g., as indicated by user input received through a user interface) can also be considered for evaluation, regardless of the number of patients in which these features appeared (might be <10%).

Identifying one or more patient characteristics can include assessing clinical and commercial feasibility of the patient characteristics. For example, patient characteristics that show a distinct clinical diagnosis can be identified. Commercial assessment can be based on data indicating forecast sales and competitor assets were available, a determined link to the targeted signal pathway (whether found or not in publications), worldwide prevalence of the patient characteristic, and the disability-adjusted life year (DALY) of the patient characteristic (e.g., per 100,000 life years). In some implementations, at least one of the one or more patient characteristics may be identified as a target indication for the drug for which new indications are to be identified. As a result, in some implementations, the one or more operations generally output one or more new indications for the drug for which new indications are to be identified.

While this specification generally describes a patient as a human patient, implementations are not so limited. For example, a patient can refer to a non-human animal, a plant, or a human replica system.

While, for illustrative purposes, this specification generally describes receiving data corresponding to approximately 94 million patients, it is understood that the data can correspond to fewer or more patients.

While, for illustrative purposes, this specification describes the drug for which new indications are to be identified as Dupilumab, it is understood that the drug for which new indications are to be identified can be any drug.

Figure 2:
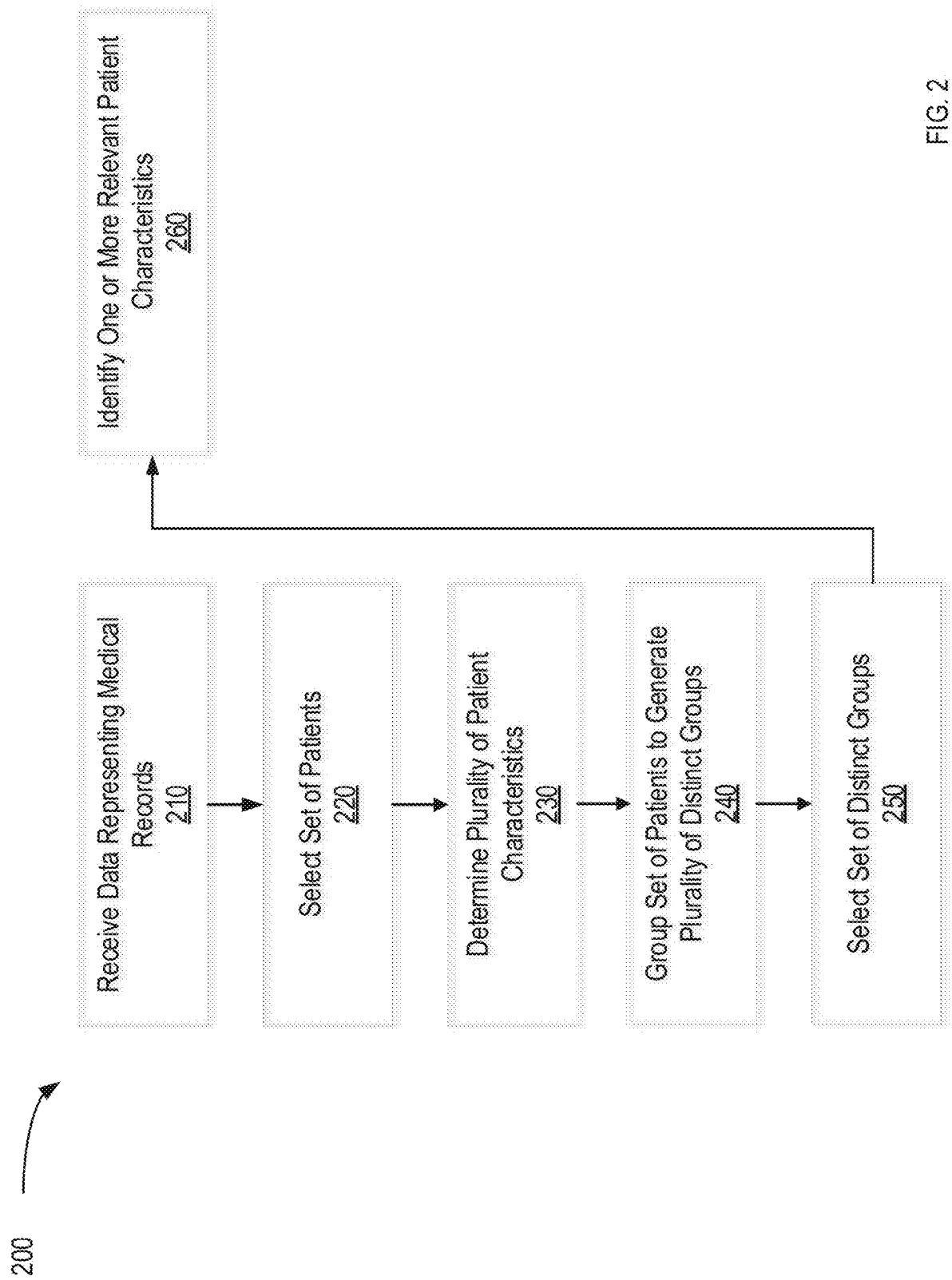
FIG. 2 is a flow chart illustrating an example method for identifying new indications for drugs.

FIG. 2 is a flow chart illustrating an example method 200 for identifying new indications for drugs. The method 200 can be performed by the data processing system 100 described previously with reference to FIG. 1. The method 200 includes receiving data representing medical records (block 210), selecting a set of patients (block 220), determining a plurality of patient characteristics (block 230), grouping the set of patients to generate a plurality of distinct groups (block 240), selecting a set of distinct groups (block 250), and identifying one or more relevant patient characteristics (block 260).

At block 210, data representing medical records of a plurality of patients is received. The data can be received from, for example, a database that includes EMRs for approximately 94 million patients (or more) identifiable by a key ID that allows matching of patients across different data tables. In some implementations, the data indicates diagnosis, lab test, procedures, medications, patient events, insurance, biomarkers, measurements, clinical status, lifestyle parameters, microbiology, prescriptions, medical images, and so forth. In some implementations, the data includes natural language process driven data. The data can be received through any of various techniques, such as wireless communications, optical fiber communications, USB, CD-ROM, and so forth.

At block 220, at least one target signaling pathway associated with the drug for which new indications are to be identified is determined. For example, if the drug is Dupilumab, it can be determined that the drug modulates the interleukin 4 (IL-4) and interleukin 13 (IL-13) signaling pathway based on known functions of the drug. In some implementations, one or more indicators are determined based on one or more factors corresponding to a diagnosis linked to the target signaling pathway. For example, factors such as pathway mechanisms, related clinical conditions, therapeutic analogues, data and epidemiology, and pharmaceutical life-cycle management alignment can be used to search through sources that include medical databases and medical evidence software to identify diseases linked to the determined signaling pathway. These diseases can be categorized based on the strength of the link to the determined signaling pathway. The categories can include a focused group, a medium group, and a broad group. For example, returning to the IL-4/IL-13 example, a focused group of diseases can include diseases that have a direct relationship with the IL-4/IL-13 mechanism of action on the Th2 pathway, a medium lens group of diseases can include diseases that have indirect relationship with the IL-4/IL-13 mechanism of action on the Th2 pathway, and a broad group of diseases can include diseases associated with a broader inflammatory response. Moving from the focus group to the broad group can increase the number of indicators to be considered when selecting the set of patients, and can reduce the likelihood of molecule impact. Accordingly, in some implementations, only the focused group, or the focused and medium group, are used to select the set of patients. In some implementations, only patients with at least one diagnosis, medication, lab test, and/or procedure associated with the determined signaling pathway are selected for inclusion into the set of patients.

At block 230, a plurality of patient characteristics of the set of patients is determined, in which each patient of the set of patients exhibits at least one of the plurality of patient characteristics. Determining the plurality of patient characteristics can include analyzing the initially received data to identify broad patient characteristics to capture all or a substantial portion of the received data. For example, the broad patient characteristics can correspond to diagnoses (e.g., immuno-conditions, diabetes), prescriptions (e.g., immuno-drugs, other drug classes), procedures (e.g., human leukocyte antigen typing), and laboratory results (e.g., IgE abnormal high/low). In some implementations, determining the plurality of patient characteristics includes receiving user input (e.g., through a user interface). For example, a user can input patient characteristics based on clinical input and demographics, medication, comorbidities, procedures and laboratory tests data specific to immunology. Bespoke characteristic classes may also be added to increase data completeness, representativeness, and to collect more information on diseases and drug response. In some implementations, determining the plurality of patient characteristics includes validating the plurality of patient characteristics. Validating can include determining whether the patient characteristics of the initially received data are mapped correctly to the selected set of patients by calculating the percentage of selected patients with at least one of each characteristic family (e.g., the percentage of patients with a prescription record) and comparing this percentage to the percentage of patients of the initially received data with at least one of each characteristic family. The two numbers being closer in value indicates that the mapping has been done correctly. Validating can include determining whether the patient characteristics have been mapped to the correct patient by identifying a number of patients that are included in both the initially received data and the selected set of patients to verify identical mapping of patient characteristics between the patients of the initially received data and the selected set of patients.

At block 240, the set of patients are grouped in accordance with the plurality of patient characteristics (e.g., as defined by features related to the determined signaling pathway) to generate a plurality of distinct groups in which each of the distinct groups include at least one patient of the set of patients. For example, clustering techniques, such as the bisecting k-means clustering technique described above, can be performed on the set of patients using the plurality of patient characteristics. The clustering can result in a plurality of clusters (e.g., distinct groups) of patients in which patients in one cluster are more similar to each other than patients in other clusters with respect to their corresponding patient characteristics. In some implementations, the generated clusters may show correlations among patient characteristics, even if they weren't present in the same patient. Clinical inputs can be received and used in various stages of the clustering process to ensure the clinical relevance of the resulting clusters. For example, disease experts' clinical inputs can facilitate the creation of clinically relevant cohorts, in the inclusion and grouping of clinically relevant features, and in validating and assessing the clusters. Patient characteristics can be identified as being distinctive in clusters if they occurred more frequently than in the general population (e.g., overall in the selected set of patients).

In some implementations, Multiple Correspondence Analysis (MCA) is used to reduce the dimensions of the patient characteristics. Bisecting K-means can facilitate an appropriate and effective separation of patients with sufficiently "tight" but stable clusters, and allow a large number of clusters that exhibited immuno-relatedness to be used for scoring the patient characteristics, which is explained later in more detail. The resulting clusters can be presented (e.g., through a user interface) to users (e.g., clinical experts) for validation and assessment. This can reduce the risk of non-interpretability of the clusters and to ensure the absence of overlapping features between the different clusters.

At block 250, a set of distinct groups of the plurality of distinct groups is selected based on or more group selection criteria. In some implementations, selecting the set of distinct groups includes ranking the groups and selecting a number of the most highly ranked groups (e.g., the top 60 ranked groups). The groups can be ranked based on immunology enrichment, stability, purity, and size. In some implementations, one or more measures are calculated for each patient characteristic to rank the clusters. The one or more measures can include, for example, distinctiveness (sometimes referred to as "lift score" in this specification), the number of patients within a cluster that present the patient characteristic, and an immunology score. The distinctiveness score measure how distinctive a patient characteristic is within a cluster versus the rest of the population (e.g., if males represent 50% of the population and 75% of the cluster, then the "lift score" can be equal to 1.5). In some implementations, only patient characteristics with a lift score that exceeds a threshold lift score (e.g., 1) and appearing in a percentage of patients that exceed a threshold percentage of patients (e.g., 10%) are considered to define clusters and correspond to a theme of the clusters. Patient characteristics that are considered to define a cluster may be referred to as potentially relevant patient characteristics in this specification. The patient characteristics (e.g., either the considered patient characteristics for defining clusters or all of the patient characteristics) can then be given an immunology score, which scores the patient characteristics according to its type (e.g., disease, drug, laboratory test, procedure, and so forth) and immunology relevance. The patient characteristic scores within each cluster can then be aggregated (e.g., summed) and normalized. Clusters meeting a threshold cluster score (e.g., 50%) can then be considered as immunology-specific.

Selecting the set of distinct groups can include assessing one or more of the stability, purity, and the number of patients within each cluster. Stability can be assessed using one or more of the following methods: (1) reproducing the clusters on different sizes of data; (2) changing the initializing seeds of the clusters; (3) changing the number of clusters produced and (4) applying a training-test method. For each cluster in the training set, stability can be defined as the maximum proportion of patients that are also grouped together in the test set. Purity can be measured by the intra-cluster variance of MCA components of patients within a cluster, which can result in homogenous and dense clusters. In some implementations, a cluster is selected if it exceeds a threshold stability percentage (e.g., 50%) and exceeds a threshold purity percentage (e.g., the cluster is in the highest 20% of purity among all clusters).

At block 260, one or more relevant patient characteristics are identified by analyzing each distinct group of the set of distinct groups. Identifying one or more relevant patient characteristics can include ranking the patient characteristics presented by each selected cluster (e.g., all of the patient characteristics or the patient characteristics considered to define a cluster). The ranking can be based on the frequency of co-occurrence with each a number of established (reference) characteristics (referential) of the drug for which new indications are to be identified (e.g., if the drug is Dupilumab, the reference characteristics may include asthma, atopic dermatitis, IgE allergy, and a composite immunology score). The co-occurrence can be measured by calculating the proportion of patient-weighted clusters that contain both the patient characteristic and the referential. In some implementations, one or more patient characteristics judged by subject-matter experts as relevant to the core cluster theme (e.g., as indicated by user input received through a user interface) can also be considered for evaluation, regardless of the number of patients in which these features appeared (might be <10%).

Identifying one or more patient characteristics can include assessing clinical and commercial feasibility of the patient characteristics. For example, patient characteristics that show a distinct clinical diagnosis can be identified. Commercial assessment can be based on data indicating forecast sales and competitor assets were available, a determined link to the targeted signal pathway (whether found or not in publications), worldwide prevalence of the patient characteristic, and the disability-adjusted life year (DALY) of the patient characteristic (e.g., per 100,000 life years). In some implementations, at least one of the one or more patient characteristics may be identified as a target indication for the drug for which new indications are to be identified.

Experimental Results

Figure 3:
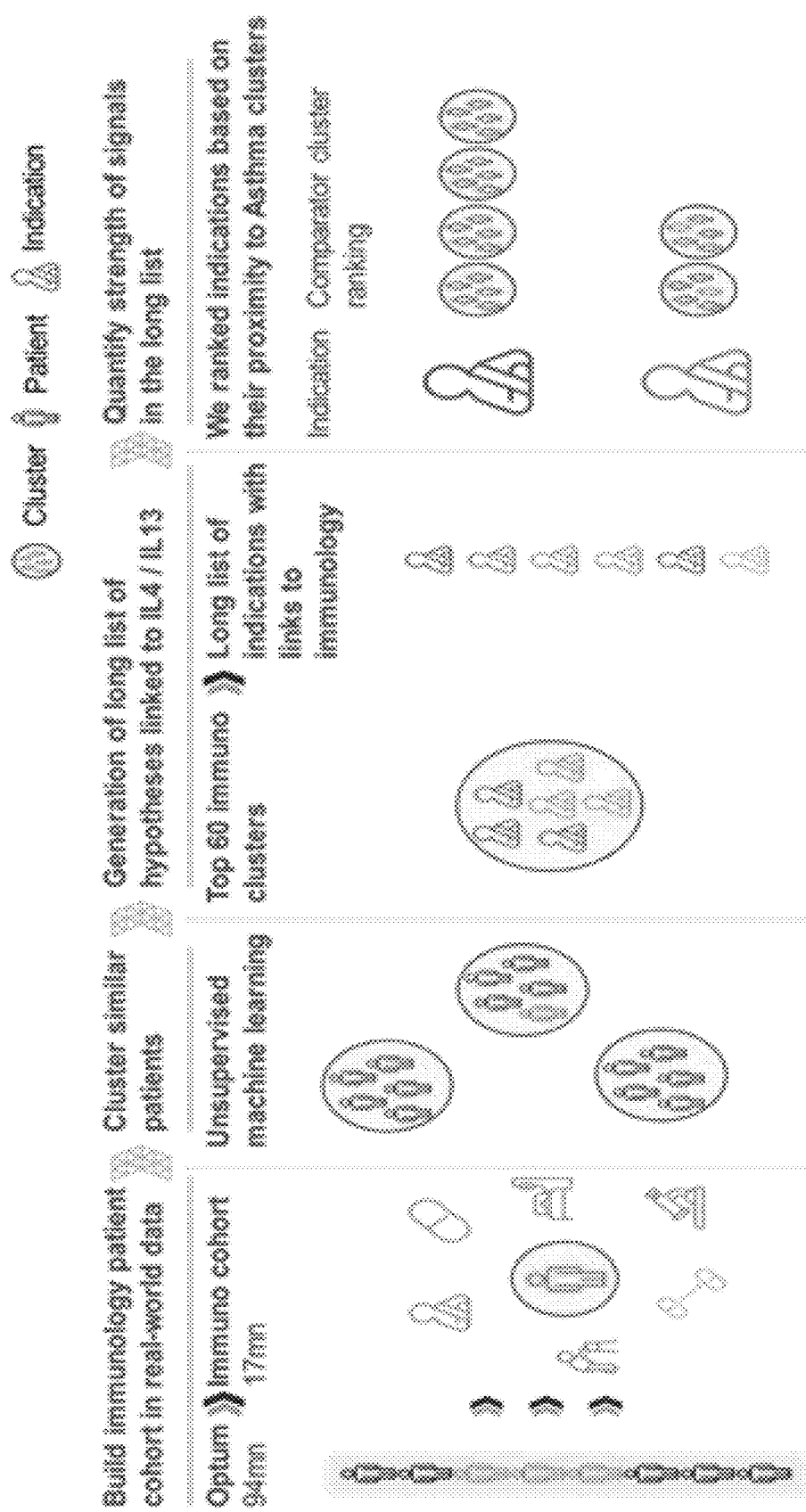
FIG. 3 is a diagram illustrating an experiment using the systems and methods described in this specification.

FIG. 3 is a diagram illustrating an experiment using the systems and methods described in this specification. The experiment was conducted to validate a RWD-driven protocol for identifying new indications of the drug Dupilumab, which is an anti-IL4/IL13 drug, in order to identify novel indications of the drug. One goal of the experiment was to reduce drug development cost and time to market, while minimizing attrition and risk. A hybrid approach was applied using scientific and clinical competences through KOL expertise, commercial assessment, and analytics combined with real world data.

Data Source: The Optum Humedica dataset for the years 2014 to 2018 was used. The database contained electronic medical records for 94 million patients identifiable by a key identifier, that allowed matching of patients across different data tables. The database collected information on EMR data, such as diagnoses, lab tests, procedures, medications, patient events, insurance, biomarkers, measurements, clinical status and lifestyle parameters, microbiology, and prescriptions. Natural Language Processing (NLP)-driven tables were not included, due to limited data coverage and clinical relevance. Furthermore, data tables that were incomplete or contained irrelevant information were excluded. A total of 5 data tables were included which reduced the data source to 40 million patients.

Selection of Patients: Indicators for patient selection were based on the clinical framework related to the underlying immunology pathways, as shown in Table 1.

TABLE 1

The 5 factors used to identify indications to consider for patient selection

| Factor | Focused lens - Th2 dysfunction causing disease | Medium lens - Th2 response associated with disease | Broad lens - Th2 response plausibly associated with disease |
|---|---|---|---|
| Pathway mechanisms | Eosinophilia<br>IL-4 pathway<br>IL-5 pathway<br>IL-13 pathway | Hypersensitivity type 1<br>Hypersensitivity type 4<br>Pruritus | Correlated autoimmune conditions<br>Other autoimmune and/or inflammatory pathways<br>End organ inflammatory conditions (e.g., cardio inflammatory, respiratory, renal)<br>Oncology pathways |
| Related clinical conditions | Eosinophilic esophagitis<br>Eosinophilic granulomatosis with polyangiitis (Churg-Strauss Syndrome) | Anaphylaxis<br>Allergic conjunctivitis<br>Urticaria | Thyroiditis<br>Pancreatitis<br>Amyloidosis<br>Basel cell carcinoma |
| Therapeutic analogues | IL-4 inhibitors<br>IL-5 inhibitors<br>IL-13 inhibitors | Downstream pathway modulators<br>JAK inhibitors<br>STAT inhibitors<br>GATA inhibitors<br>IL-25<br>Upstream pathway modulators<br>IL-2 inhibitors | Other pathway determining interleukin targets: IL-1, IL-6, IL-12, IL-21, IL-23<br>Downstream interleukin targets: IL-9, IL-17, IL-22<br>Other potential proinflammatory targets: IFN, TGFβ, TNFα |
| Data and epidemiology | Eosinophilic conditions | Hypersensitivity type 1 conditions | Autoimmune conditions<br>Inflammatory conditions<br>Oncology diseases |
| LCM strategy alignment | Eosinophilic esophagitis<br>Adjunctive therapy for peanut and grass allergy | Chronic rhinosinusitis<br>Chronic spontaneous urticaria<br>Atopic keratoconjunctivitis | |

Only adult patients (aged≥18 years old) with at least one diagnosis, medication, lab test and procedure who ever suffered from an IL4/13 pathway (i.e., signaling pathway) associated diagnosis were selected. Using these criteria of immunology conditions and data completeness, the resulting cohort consisted of 17 million unique patients.

The five factors (as shown in table 2) were considered for identifying indicators. These factors were searched through sources on Doctor Evidence engine database, a medical evidence software and services company, composed of several platform (DOC Library, DOC Data, Doctor Evidence, DOC Label, DOC Search) and including PubMed, ClinicalTrials.gov, WHO, and so forth. Information within these factors was then classified according to three lenses based on Th2 response: focused, medium and broad. For example, diseases were allocated to the focused or medium lens based on their direct and indirect relationship with IL4/IL13 mechanism of action on the Th2 pathway respectively, and to the broad lens if they were associated with a broader inflammatory response. Moving from the focused to the broad lens increased the range of indicators to be considered and reduced the likelihood of molecule impact. Indicators in the broad lens were eventually excluded from the analysis as their mechanistic link wasn't specific enough to meet criteria for identifying patient populations with similar characteristics. Hence, only indicators for the focused and medium lenses were included in the experiment. A final list of 208 indicators were included for analysis across 17 broad systems.

Selection of features: Broad features (patient characteristics) were selected to capture the available information in the Optum dataset; then, features selected by clinical experts were prioritizes and validated to ensure that all essential variables were included, and the variable values made clinical sense. When appropriate, certain features were retained while others (certain demographics) were created de novo (as shown by V1 as described later with reference to FIG. 4). New features were added based on clinical input and demographics, medication, comorbidities, procedures and laboratory tests data specific to immunology. Bespoke feature classes were created and added to the analysis iteratively (as shown by V2 and V3 as described later with reference to FIG. 4) to increase data completeness, representativeness, and collect more information on the severity of the disease and drug response.

A robust approach was used to ensure the completeness of the features in the final database. Two validation steps, based on patient and feature mapping across the Optum database and the generated table, were taken to verify that the features were generated correctly. First, to validate whether the patient features in Optum mapped to our data table correctly, the percentage of patients with at least one feature family was calculated and it was determined whether this number was identical in Optum Humedica and our data table. Second, to validate whether the features mapped to the correct patient, ten random patients were tracked from the raw Optum Humedica data to the generated dataset, to ensure identical mapping of features in the two datasets. After the feature validation had demonstrated the correct mapping, the algorithm was run on 17 million patients with 2700 features included.

Clustering: A clustering technique was used to group patients together that share similar characteristics as defined by features related to the IL4/13 pathway. The clustering looked for similarities between patients based on their features. The generated clusters resulted in finding correlations among conditions, even if they weren't present in the same patient. Clinical inputs were embedded in various stages of the process to ensure the clinical relevance of the results. Thus, disease experts' clinical inputs assisted in the creation of clinically relevant cohorts, in the inclusion and grouping of clinically relevant features and finally in the cluster validation and assessment. Features were identified as being distinctive in clusters if they occurred more frequently than in the general population.

Multiple Correspondence Analysis (MCA) was used to reduce the dimensions of the features. Bisecting K-means was then utilized to split the data into 500 clusters, to provide an appropriate and effective separation of patients with sufficiently 'tight' but stable clusters and allow a large number of clusters that exhibited immuno-relatedness to be used for the indication scoring. The clusters identified through the process were validated and assessed by clinical experts. This step facilitated the reduction in risk of non-interpretability of the clusters and ensured the absence of overlapping features between the different clusters. The clustering approach ran data representing 2700 features (e.g., the MCA components) and 17 million patients. The number of clusters produced at the end of the algorithm was 500.

Identification of new indications (i.e., relevant patient characteristics): Further assessment, clinical and commercial judgement were performed to obtain a short list of priority signals and identify the most clinically relevant indications across clusters based on the cluster outputs. Four methodological steps were used. The first one selected the top 60 clusters among the 500 ranked, based on immunology enrichment, stability, purity, and size. Three measures were calculated for the features included in each cluster to determine the selection: distinctiveness, the number of patients presenting the feature within each cluster, and the immunology score. The distinctiveness, also called "lift score", measured how distinctive a feature is within a cluster versus the rest of the population (e.g. if males represent 50% of the population and 75% of the cluster, then the lift score is equal to 1.5). Only the features with a lift score>1 (meaning they occurred in the cluster at a higher rate than expected compared to a broader population) and appearing in ≥10% of the patients were considered for defining (and naming) a cluster and developing themes of clusters. In addition, each selected feature was given a score according to its type (disease, drug, laboratory test or procedure) and immunology relevance. The features scores within each cluster were summed up and normalized. The clusters were then considered as immunology-specific if they met a pre-defined threshold of the score of 50%. As a second step, the clusters were selected according to stability, purity, and the number of patients. The stability was assessed using four methods: 1. reproducing the clusters on different sizes of data, 2. changing the initializing seeds of the clusters, 3. changing the number of clusters produced and 4. applying a train-test method. For each cluster in the train set, stability is defined as the maximum proportion of patients that are also grouped together in the test set. Purity was measured by the intra-cluster variance of MCA components of patients within that cluster, resulting in homogenous and dense clusters. A cluster is included in the analysis if it has more than 50% stability and is in the highest 20% of purity. In addition, all the indications judged by subject-matter experts as relevant to the core cluster theme were considered for evaluation, regardless of the number of patients in which these features appeared (might be <10%). These new indications were then ranked based on the frequency of co-occurrence with each of the four established indications (referential) of dupilumab (asthma, atopic dermatitis, IgE allergy, and the composite immunology score) in the third step. The co-occurrence was measured by calculating the proportion of patient-weighted clusters that contain both the indication and the referential. In the last step, the final list of indications was further characterized by clinical and commercial feasibility. The clinical assessment retained the indications that showed a distinct clinical diagnosis. Based on the ranking with the IL4/IL13 referential, conditions that did not appear in the top 30 were deleted as they looked to be poorly related to IL4/IL13 modulation. The commercial assessment was possible only for a subset of clinical plausible indications, where the data on forecast sales and competitor assets were available. In addition, multiple factors were also considered for the commercial assessment: the link to IL4/13 pathway whether found or not in the literature, the worldwide prevalence of the indication and the disability-adjusted life year (DALY) of the indication (per 100,000 life years).

Figure 4:
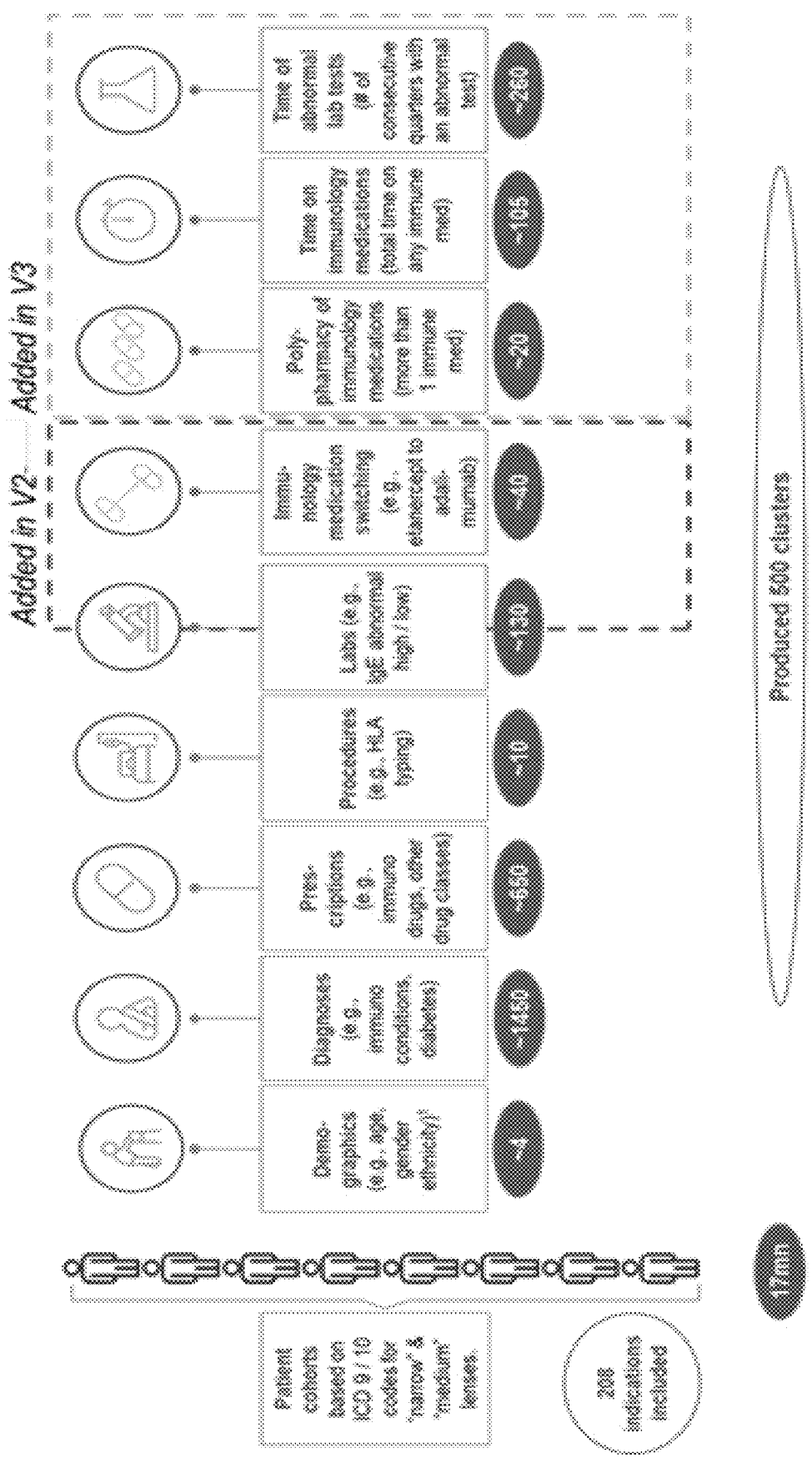
FIG. 4 is a diagram illustrating experimental results resulting from the use of the systems and methods described in this specification.

Results: FIG. 4 is a diagram illustrating experimental results resulting from the use of the systems and methods described in this specification. The final cohort of 17 million patients, extracted from Optum Humedica, was analyzed to assess data completeness and representativeness across the selected features. In the medium lens population, the cohort of patients was composed of 59% females, mostly Caucasian (77%), with mean age at last activity of 53 years (SD=7 years) and mean follow up period of 7.1 years. Patients presented most frequently ICD10 codes for acute sinusitis (25.2%), allergic rhinitis, unspecified (20.6%), and other and unspecified asthma (19.4%) as immunology conditions. The most frequent immunology-related medications were prednisone (28.0%), fluticasone furoate (22.2%), and methylprednisolone (13.3%), and 0.4% of patients underwent allergen immunotherapy injections and beta2 glycoprotein antibody measurement. Most of the patients were tested for white blood cell count (70.8%), absolute neutrophils count (ANC) (64.3%), and absolute lymphocyte count (ALC) (63.8%). The clustering procedure created 500 clusters, out of which 125 were classified as both enriched for immune conditions and stable. Of these 125, 110 were also classified as pure. Among these, 60 clusters containing the largest number of patients per cluster were retained and analyzed for clinically relevant signals. Following the validation process, 84% of the clusters were considered highly stable using the train-test method, 90% and 99% of the top 20 clusters were reproduced regardless of the seed position and the number of patients in data table respectively. Six cluster themes were identified based on the features included in the clusters and reproduced in part also in the V2 and V3 iterations: multi-organ immunological impact, neoplasia, asthma and other hypersensitivities, musculoskeletal dysfunction, cardiometabolic spectrum, and gynecology & maternity conditions. Among them, 250 indications were selected by cluster assessment and ranked by co-occurrence with each referential. A list of around 85 indications was further characterized by clinical and commercial feasibility: among them around 20 didn't represent a distinct clinical diagnosis or have poor clinical rationale for IL4/13 modulation, others didn't have readily commercial assessment information. The final list of indications coming from the hybrid approach identified approximately 90% of the indications already in the life-cycle management, as well as approximately 60% of additional potential new indications.

Figure 5:
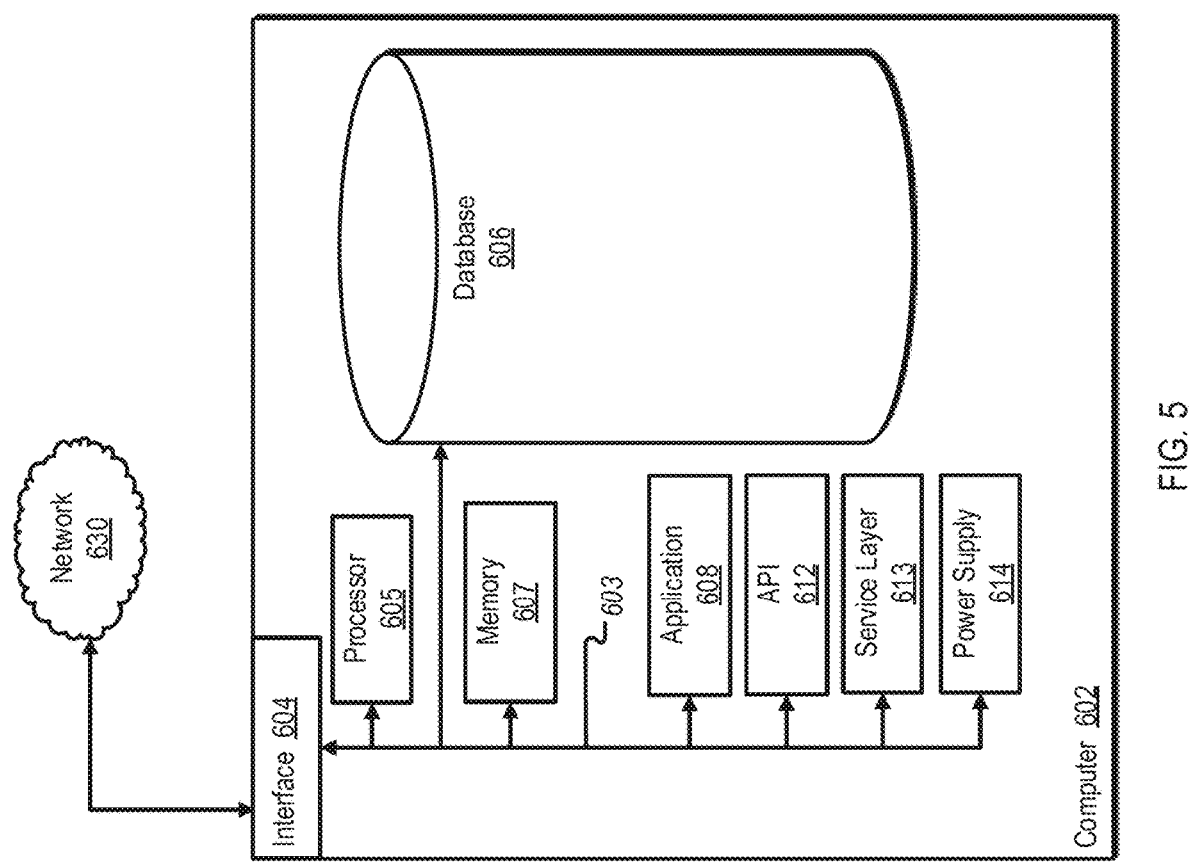
FIG. 5 is a block diagram of an example computer system used to provide computational functionalities associated with algorithms, methods, functions, processes, flows, and procedures described in the present disclosure

FIG. 5 is a block diagram of an example computer system 600 used to provide computational functionalities associated with described algorithms, methods, functions, processes, flows, and procedures described in the present disclosure (such as the method 200 described previously with reference to FIG. 2), according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 5, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 5, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 5, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 5, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising" or "further including" in the foregoing description or following claims, what follows this phrase can be an additional step or entity, or a sub-step/sub-entity of a previously-recited step or entity.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A computer-implemented method for repurposing a drug by identifying one or more new indications for the drug, comprising:
  receiving, by a computer system, data representing medical records of a plurality of patients;
  selecting, based on the medical records, a set of patients from the plurality of patients by operations comprising:
    determining at least one target signaling pathway associated with the drug; and
    determining one or more indicators based on one or more factors corresponding to a diagnosis linked to the target signaling pathway;
  determining a plurality of patient characteristics of the set of patients, each patient of the set of patients exhibiting at least one of the plurality of patient characteristics;
  grouping, by the computer system, in accordance with the plurality of patient characteristics, the set of patients to generate a plurality of distinct groups, each of the distinct groups including multiple patients of the set of patients, wherein the grouping comprises:
    executing a machine learning system configured to perform one or more unsupervised clustering techniques, wherein the one or more unsupervised clustering techniques comprise an iterative clustering operation, comprising:
      applying the iterative clustering operation to feature vectors characterizing the patients in the set of patients to optimize a clustering function, wherein the iterative clustering operation comprises a bisecting k-means clustering technique; and identifying the plurality of distinct groups based on a result of applying the iterative clustering operation to the feature vectors characterizing the patients in the set of patients; and processing data defining the plurality of distinct groups to identify one or more new indications for the drug, comprising:

selecting, based on one or more group selection criteria, a set of distinct groups of the plurality of distinct groups for use in identifying new indications for the drug, comprising:

determining, for each of the plurality of distinct groups, a stability of the distinct group under perturbations of parameters of the iterative clustering operation;

determining, for each of the plurality of distinct groups, a purity of the distinct group based on a measure of variance between feature vectors of patients included in the distinct group; and determining, for each of the plurality of distinct groups, whether to select the distinct group based at least in part on whether: (i) the stability of the distinct group under perturbations of parameters of the iterative clustering operation satisfies a first threshold, and (ii) the purity of the distinct group as determined based on the measure of variance between feature vectors of patients included in the distinct group satisfies a second threshold;

wherein fewer than all of the plurality of distinct groups are selected for use in identifying new indications for the drug;

identifying one or more relevant patient characteristics by processing data characterizing only the set of distinct groups that have been selected for use in identifying new indications for the drug; and identifying at least one of the one or more relevant patient characteristics as a new indication for the drug; and administering the druq to a patient as a treatment for the new indication, wherein the druq comprises an anti-interleukin-4 receptor alpha (anti-IL-4Rα) antibody, wherein the druq comprises Dupilumab.

2. The method of claim 1, wherein grouping the set of patients comprises performing multiple correspondence analysis to reduce dimensions of the plurality of patient characteristics.

3. The method of claim 1, wherein selecting the set of distinct groups further comprises:

determining, for each distinct group of the plurality of distinct groups, a feature score for each patient characteristic exhibited by that distinct group; and comparing the feature score of each distinct group of the plurality of distinct groups to a feature score threshold.

4. The method of claim 1, wherein selecting the set of distinct groups further comprises:

determining, for each of the plurality of distinct groups, a number of patients that are included in the distinct group; and determining, for each of the plurality of distinct groups, whether to select the distinct group based at least in part on whether the number of patients that are included in the distinct group satisfies a third threshold.

5. The method of claim 1, wherein identifying the one or more relevant patient characteristics comprises:

generating a plurality of potentially relevant patient characteristics by, for each distinct group of the set of distinct groups that have been selected for use in identifying new indications for the drug, selecting the patient characteristics of the plurality of patient characteristics that are exhibited by that distinct group and correspond to a theme of that group; and ranking each of the potentially relevant patient characteristics of the plurality of potentially relevant patient characteristics.

6. The method of claim 5, wherein ranking each of the potentially relevant patient characteristics comprises, for each potentially relevant patient characteristic, assigning a rank value based on a frequency of co-occurrence of that potentially relevant patient characteristic and at least one referential indication associated with the drug.

7. The method of claim 6, wherein the co-occurrence is measured by determining, for each of the potentially relevant patient characteristics, a proportion of the set of distinct groups that comprises both that potentially relevant patient characteristic and the at least one referential indication.

8. The method of claim 5, wherein identifying the one or more relevant patient characteristics comprises determining, for each of the potentially relevant patient characteristics, at least one of: a clinical feasibility and a commercial feasibility.

9. The method of claim 1, wherein the target signaling pathway associated with the drug is an IL4/IL13 pathway, and wherein the drug comprises an anti-interleukin-4 receptor alpha (anti-IL-4Rα) antibody.

10. The method of claim 9, wherein the drug comprises Dupilumab.

11. The method of claim 1, wherein selecting, based on the medical records, a set of patients from the plurality of patients further comprises:

selecting patients that each have one or more characteristics related to an IL4/IL13 pathway for inclusion in the set of patients.

12. The method of claim 11, wherein selecting patients that each have one or more characteristics related to the IL4/IL13 pathway for inclusion in the set of patients comprises:

selecting patients that are each associated with clinical conditions linked to the IL4/IL13 pathway for inclusion in the set of patients, wherein the clinical conditions linked to the IL4/IL13 pathway comprise one or more of: eosinophilic esophagitis, eosinophilic granulomatosis with polyangiitis (Churg-Strauss Syndrome), anaphylaxis, allergic conjunctivitis, urticaria, thyroiditis, pancreatitis, amyloidosis, or basal cell carcinoma.

13. The method of claim 11, wherein characteristics related to the IL4/IL13 pathway comprise one or more of: a diagnosis linked to the IL4/IL13 pathway, a medication linked to the IL4/IL13 pathway, a lab test linked to the IL4/IL13 pathway, or a procedure linked to the IL4/IL13 pathway.

14. The method of claim 1, wherein identifying one or more relevant patient characteristics by processing data characterizing only the set of distinct groups that have been selected for use in identifying new indications for the drug comprises:

ranking a plurality of candidate drug indications based on:
(i) the set of distinct groups that have been selected for use in identifying new indications for the drug, and (ii) one or more reference drug indications associated with the drug; and identifying one or more of the plurality of candidate drug indications as new indications for the drug based on the ranking of the plurality of candidate drug indications.

15. The method of claim 14, wherein ranking the plurality of candidate drug indications based on: (i) the set of distinct groups that have been selected for use in identifying new indications for the drug, and (ii) one or more reference drug indications associated with the drug comprises:

determining, for each candidate drug indication, a co-occurrence score that defines a frequency of co-occurrence of: (i) the candidate drug indication, and (ii) the one or more reference drug indications, among the set of distinct groups that have been selected for use in identifying new indications for the drug; and determining the ranking of the plurality of candidate drug indications based at least in part on the co-occurrence scores for the plurality of candidate drug indications.

16. The method of claim 15, wherein for each candidate drug indication, determining the co-occurrence score that defines the frequency of co-occurrence of: (i) the candidate drug indication, and (ii) the one or more reference drug indications, among the set of distinct groups that have been selected for use in identifying new indications f or the drug comprises:

determining a number of distinct groups that are associated with both: (i) the candidate drug indication, and (ii) one or more of the reference drug indications.

* * * * *

UNITED STATES PATENT AND TRADEMARK OFFICE
CERTIFICATE OF CORRECTION

| | | |
|---|---|---|
| PATENT NO. | : 12,243,628 B2 | Page 1 of 1 |
| APPLICATION NO. | : 17/116995 | |
| DATED | : March 4, 2025 | |
| INVENTOR(S) | : Bryce et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this
Twenty-ninth Day of July, 2025

Coke Morgan Stewart
*Acting Director of the United States Patent and Trademark Office*